(12) United States Patent
Konawa

(10) Patent No.: US 8,366,696 B2
(45) Date of Patent: Feb. 5, 2013

(54) ABSORBENT ARTICLE

(75) Inventor: Satoko Konawa, Sakura (JP)

(73) Assignee: DAIO Paper Corporation, Shikokuchuo-shi, Ehime (JP)

( * ) Notice: Subject to any disclaimer, the term of this patent is extended or adjusted under 35 U.S.C. 154(b) by 205 days.

(21) Appl. No.: 12/448,658

(22) PCT Filed: Dec. 27, 2007

(86) PCT No.: PCT/JP2007/075109
§ 371 (c)(1),
(2), (4) Date: Jul. 28, 2009

(87) PCT Pub. No.: WO2008/078805
PCT Pub. Date: Jul. 3, 2008

(65) Prior Publication Data
US 2010/0030175 A1    Feb. 4, 2010

(30) Foreign Application Priority Data

Dec. 27, 2006 (JP) ................. 2006-351165

(51) Int. Cl.
*A61F 13/15* (2006.01)
(52) U.S. Cl. .......... 604/385.01; 604/365; 604/367; 604/385.201; 604/385.21; 604/385.23

(58) Field of Classification Search ............. 604/365, 604/367, 385.01, 385.101, 385.201, 385.21, 604/385.23
See application file for complete search history.

(56) References Cited

U.S. PATENT DOCUMENTS 4,445,900 A * 5/1984 Roeder .................. 604/389
6,391,011 B1 * 5/2002 Davis et al. ............ 604/385.05
2005/0124953 A1   6/2005 Woltman et al.

FOREIGN PATENT DOCUMENTS

WO    WO-02/45697     6/2002
WO    WO-2005/063160  7/2005

* cited by examiner

*Primary Examiner* — Lynne Anderson
*Assistant Examiner* — Bradley Philips
(74) *Attorney, Agent, or Firm* — Jordan and Hamburg LLP

(57) ABSTRACT

An absorbent article comprises an absorbent interposed between a liquid-permeable surface sheet and a back sheet. The absorbent is constituted of a set of left and right absorbent elements arranged substantially along the longitudinal direction of the absorbent article. The absorbent element of one side is formed as a dogleg to the right in a top plan view whereas the absorbent element of the other side is formed as a dogleg to the left in a top plan view, so that the absorbent elements have an intersecting portion intersecting in at least the region containing the portion corresponding to the blood discharge opening of the wearer.

17 Claims, 14 Drawing Sheets

TRANSFER DIRECTION

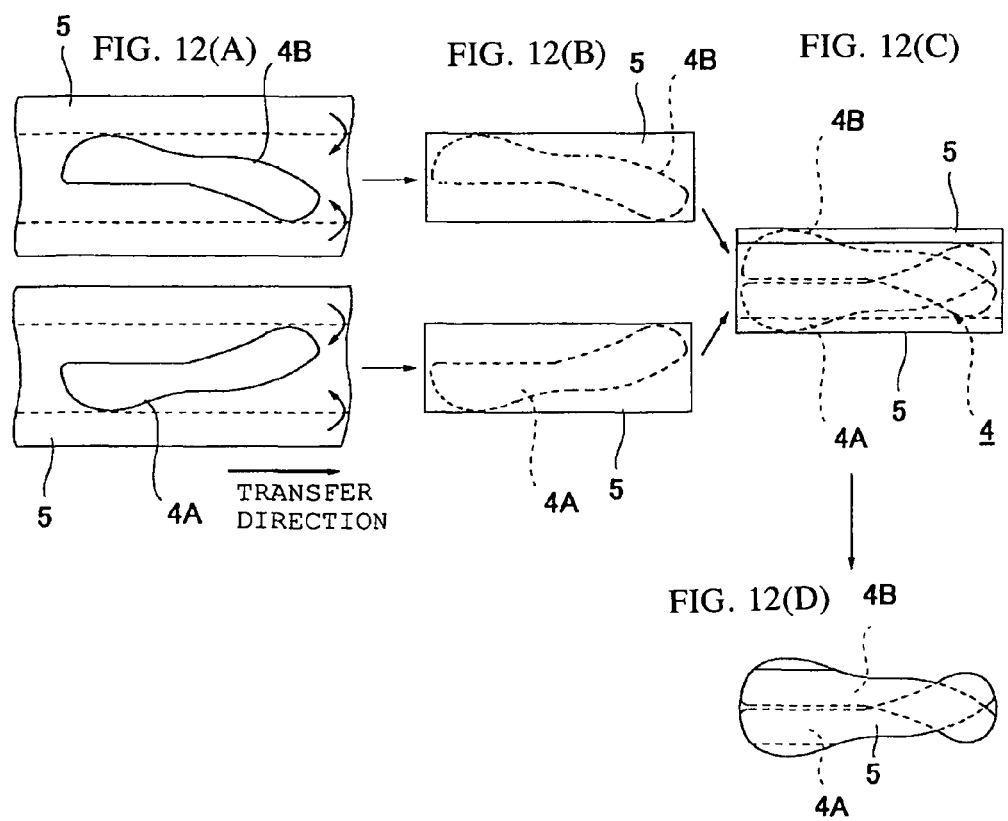

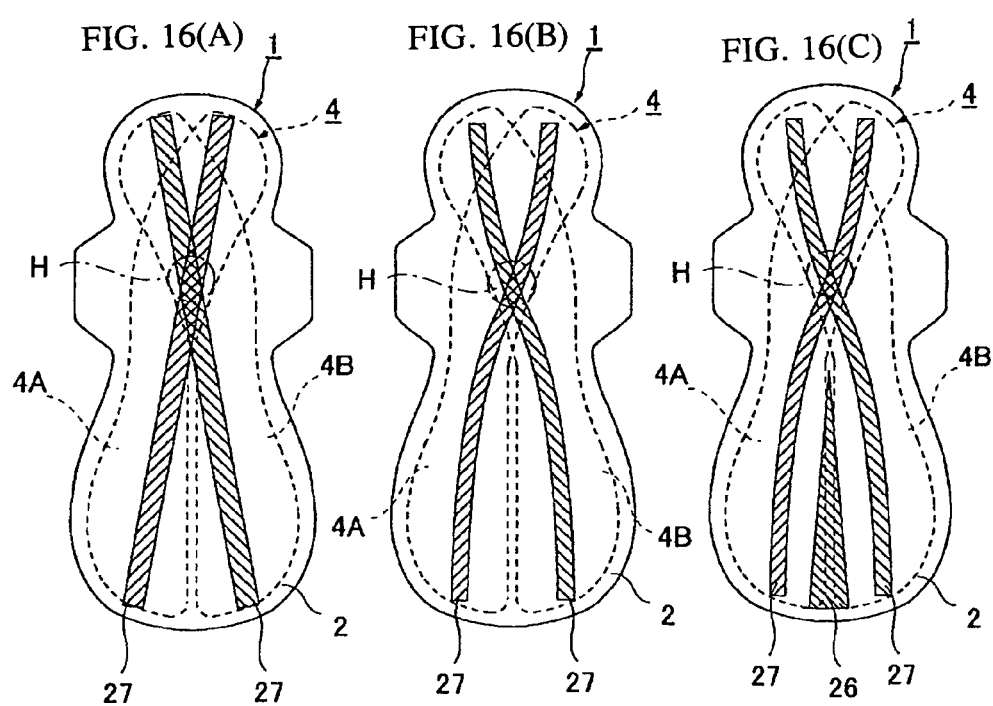

ABSORBENT ARTICLE

BACKGROUND OF THE INVENTION

The present invention relates mainly to an absorbent article to be used for a sanitary napkin, a vaginal discharge sheet, an incontinence pad, a medical pad, toiletries or the like, and to an absorbent article which fits the body and hardly gets twisted and which follows the motions of the body easily.

In the prior art, the known absorbent article such as the panties liner, the sanitary napkin or the incontinence pad is prepared by interposing an absorbent made of cellulose wadding such as pulverized pulp between a liquid-impermeable back sheet such as a polyethylene sheet or a polyethylene laminated nonwoven fabric and a liquid-permeable surface sheet such as nonwoven fabric or a liquid-permeable plastic sheet.

With a view to preventing the leakage of a body liquid or the like, those absorbent articles are known to have means for improving the fitness properties on various bodies, as disclosed in the following Patent Documents 1 and 2. Specifically in Patent Document 1, a plurality of embossed grooves are formed into the absorbent from the upper face of the same so that the absorbent may be folded along the curve of the body of the wearer. Thus, the absorbent is improved in its fitness to the curved body surface thereby to prevent the leakage.

In Patent Document 2, on the other hand, the absorbent is provided on the side of its skin abutting face with a crown portion, which is narrower than the absorbent and bulges. This crown portion is composed of a front crown portion and a back crown portion, which are formed separately of each other in front of and at the back of the absorbent article. Between these front and back crown portions, there is formed a fold starting point, which prevents the deformations of the front portion and the back portion from influencing each other. As a result, the deformations of the front portion and the back portion are kept away from any mutual influence.

Patent Document 1: JP-A-2006-149413
Patent Document 2: JP-A-2006-239162

SUMMARY OF THE INVENTION

In the absorbent article described in Patent Documents 1 and 2, however, the crown portions formed on the surfaces of the absorbent can improve the fitness on the body. A torsional deformation may be caused in the entirety of the absorbent article at the wearing time by the motions of buttocks occupying a wide area in the body portion covered with the absorbent article. In this case, a twist is made in the crown portions which have contacted the body liquid discharge portion closely, and the fitness may be lost to leak out the body liquid.

Therefore, a main object of the invention is to provide an absorbent article, which can have an excellent followability, when worn, to the motions of the body, especially such body motions as might otherwise cause a torsional deformation, and which can fit the body so that it can prevent the leakage accordingly reliably.

In order to solve the problems, according to a first aspect of the invention, there is provided an absorbent article comprising an absorbent interposed between a liquid-permeable surface sheet and a back sheet, characterized in that the absorbent is constituted of a set of left and right absorbent elements arranged substantially along the longitudinal direction of the absorbent article and arranged to intersect at a region containing a portion corresponding to at least the blood discharge opening of a wearer.

In the first aspect of the invention, the absorbent is constituted of a set of left and right absorbent elements arranged substantially along the longitudinal direction of the absorbent article and arranged to intersect at a region containing a portion corresponding to at least the blood discharge opening of a wearer. Even if the absorbent article is torsionally deformed, moreover, the easy deformations from the intersecting portion in the oblique direction cause the individual absorbent elements to follow the motions of the body. At the intersecting portion, moreover, the individual absorbent elements are arranged to overlap and to retain a sufficient thickness, so that they hardly get twisted but can fit the blood discharge opening better. Thus, the absorbent article can retain the body liquid absorbing performance thereby to prevent the leakage reliably.

According to a second aspect of the invention, there is provided an absorbent article comprising an absorbent interposed between a liquid-permeable surface sheet and a back sheet, characterized in that the absorbent is constituted of a set of left and right absorbent elements arranged substantially along the longitudinal direction of the absorbent article, and in that the absorbent element of one side is formed into such a flat shape as is dogleg to the right in a top plan view whereas the absorbent element of the other side is formed into such a flat shape as is dogleg to the left in a top plan view, so that the absorbent elements are arranged to intersect each other in at least the region containing the portion of the blood discharge opening of the wearer.

The second aspect of the invention presents the specific embodiment, the individual absorbent elements are formed into the flat shape, in which the absorbent elements are symmetrically bent in the top plan view so that the absorbent having the intersecting portions can be realized. Here, it is desired for the costs of the pulp stacking facilities and the transfer lines that the individual absorbent elements are made to have identical shapes and are manufactured by reversing each other.

In a third aspect of the invention, there is provided an absorbent article of the first or second aspect of the invention, wherein the individual absorbent elements are so arranged in parallel at the back portion of the absorbent article that they have no portion overlapping each other at the widthwise central portion along the longitudinal direction.

In the third aspect of the invention, the individual absorbent elements are so arranged in parallel at the back portion of the absorbent article that they have no portion overlapping each other at the widthwise central portion along the longitudinal direction. As a result, the resistance to the torsional displacement of the absorbent is lightened so that the absorbent article can follow the motions of the body easily thereby to prevent the twist of the absorbent. Moreover, the widthwise central portion of the back portion of the absorbent article can be easily mountain-folded, when fitted in the groove of the buttocks, toward the using face side along the longitudinal direction.

In a fourth aspect of the invention, there is provided an absorbent article of the first or second aspect of the invention, wherein the individual absorbent elements are arranged to have such an overlap portion at the back portion of the absorbent article that they overlap each other at the widthwise central portion along the longitudinal direction.

In the fourth aspect of the invention, the individual absorbent elements are arranged to have such an overlap portion at the back portion of the absorbent article that they overlap each other at the widthwise central portion along the longitudinal direction. The overlap portion can prevent the body liquid on the back side from flowing from the clearance between the absorbent elements to the side of the back sheet.

In a fifth aspect of the invention, there is provided an absorbent article of any of the first to fourth aspects of the invention, wherein the portion corresponding to the crotch of the wearer is the narrowest.

In the fifth aspect of the invention, the portion corresponding to the crotch of the wearer is the narrowest. As a result, the absorbent can fit the legs of the wearer with no uncomfortable feeling.

In a sixth aspect of the invention, there is provided an absorbent article of any of the first to fifth aspects of the invention, wherein the individual absorbent elements are arranged to overlap substantially coextensively in the region of the absorbent article on the front side of the portion corresponding to the blood discharge opening of the wearer.

In the sixth aspect of the invention, the individual absorbent elements are arranged to overlap substantially coextensively in the region of the absorbent article on the front side of the portion corresponding to the blood discharge opening of the wearer. As a result, the front portion can absorb the body liquid more and can be more rigid at its front portion. As a result, the absorbent article is prevented from getting twisted so that it can be improved in close contact with the body.

In the seventh aspect of the invention, there is provided an absorbent article of any of the first to sixth aspects of the invention, wherein the individual absorbent elements are made thinner at an outer edge portion in the front side portion of the absorbent article and at an inner edge portion in the back side portion of the absorbent article than the remaining portions.

In the seventh aspect of the invention, the individual absorbent elements thus formed are arranged to intersect with each other, so that the absorbents at the portions around the legs and along the groove between the buttocks are made thin. When the absorbent article is worn, no uncomfortable feeling is given around the legs of the wearer, and the absorbent article is easily folded and clamped in the groove between the buttocks.

In an eighth aspect of the invention, there is provided an absorbent article of any of the first to seventh aspects of the invention, wherein the corners of the back end portions of the sides confronting the paired absorbent elements are cut off so that a notch is formed at the center of the back end portion of the absorbent.

In the eighth aspect of the invention, the notch can be easily pinched by the fingers of the wearer and fitted in the groove between the buttocks thereby to lighten the wearing troubles.

In a ninth aspect of the invention, there is provided an absorbent article of any of the first to eighth aspects of the invention, wherein an elastic member is arranged at the absorbent center along the longitudinal direction at the back side portion of the absorbent article between the back sheet and the absorbent.

In the ninth aspect of the invention, the elastic member is arranged so that the back side portion of the absorbent article may be deformed along and easily fitted in the groove between the buttocks.

In a tenth aspect of the invention, there is provided an absorbent article of any of the first to ninth aspects of the invention, wherein a hydrophilic second sheet is arranged at the widthwise center along the longitudinal direction.

In the tenth aspect of the invention, the second sheet is arranged so that the body liquid from the front side portion of the blood discharge opening to the buttocks may be quickly absorbed, thereby to prevent the leakage of the body liquid.

In the eleventh aspect of the invention, there is provided an absorbent article of any of the first to tenth aspects of the invention, comprising stereo gathers raised from the two side portions of the using face of the absorbent article by the shrinking forces of elastic stretching members, wherein the stereo gathers are raised within the ranges corresponding to the intersecting portion of the individual absorbent elements.

In a twelfth aspect of the invention, in order to prevent the transverse leakage of the body liquid reliably with the necessary minimum material and to improve the followability on the back side, there are disposed the stereo gathers which rise only within the range corresponding to the intersecting portion of the individual absorbent elements.

In the twelfth aspect of the invention, there is provided an absorbent article of any of the first to eleventh aspects of the invention, wherein the individual absorbent elements are individually enclosed by the crepe papers.

In the twelfth aspect of the invention, the individual absorbent elements are individually enclosed by the crepe papers so that they may be easily deformed according to the motions of the body.

In a thirteenth aspect of the invention, there is provided an absorbent article of any of the first to eleventh aspects of the invention, wherein the individual absorbent elements are not enclosed by the crepe papers but are interposed directly between the surface sheet and the back sheet.

In the thirteenth aspect of the invention, the individual absorbent elements are not enclosed by the crepe papers but are interposed directly between the surface sheet and the back sheet. As a result, the hardening of the absorbent, as might otherwise be caused by enclosing it with the crepe papers, can be prevented so that the followability to the motions of the body is not obstructed. Moreover, no crepe paper is interposed so that the body liquid is quickly transferred from the surface sheet to the absorbent.

In a fourteenth aspect of the invention, there is provided an absorbent article of any of the first to thirteenth aspects of the invention, wherein the individual absorbent elements are joined to each other by embossing at the intersecting portion between the individual absorbent elements from the upper face side.

In the fourteenth aspect of the invention, the joint of the individual absorbent elements is performed by embossing at the intersecting portion from the upper side so that a high joint strength can be attained. Even if a torsional deformation of the absorbent occurs at the back portion of the absorbent article, the twist can be reliably prevented at the intersecting portion which might otherwise become the starting point.

In a fifteenth aspect of the invention, there is provided an absorbent article of any of the first to fourteenth aspects of the invention, comprising a plurality of stripes of pressure-sensitive adhesive layers formed on the outer face of the back sheet so that they may be adhered to the shorts, wherein one of the plural stripes of the pressure-sensitive adhesive layers is formed along the longitudinal direction at the widthwise central portion in the back side portion of the absorbent article.

In the fifteenth aspect of the invention, there is considered the case, in which the widthwise central portion in the back side portion of the absorbent article is inserted in a mountain-fold into the groove between the buttocks. In this case, one of the plural stripes of the pressure-sensitive adhesive layers on the back face side is formed along the longitudinal direction at the widthwise central portion in the back side portion of the absorbent article. When the absorbent article is mountain-folded by pinching the widthwise central portion by the fingers of the wearer, the pressure-sensitive adhesive layers are adhered to each other so that the valley-fold is maintained.

In a sixteenth aspect of the invention, there is provided an absorbent article of any of the first to fifteenth aspects of the invention, comprising at least two stripes of pressure-sensitive adhesive layers formed on the outer face of the back sheet and adapted to be adhered to the shorts, wherein the pressure-sensitive adhesive layers extend along the individual absorbent elements and intersect with each other at the portion corresponding substantially to the blood discharge opening of the wearer.

In the sixteenth aspect of the invention, the left and right pressure-sensitive adhesive layers of one set extend along the individual absorbent elements and intersect with each other at the portion corresponding substantially to the blood discharge opening of the wearer. As a result, the pressure-sensitive adhesive layers do not obstruct the motions of the absorbent to accompany the torsional deformations of the body. Moreover, pressure-sensitive adhesive layers are formed along the absorbent elements so that they can prevent the displacements from the shorts.

According to the invention, as has been described hereinbefore, the absorbent article can have an excellent followability, when worn, to the motions of the body, especially such body motions as might otherwise cause a torsional deformation, and can fit the body so that it can prevent the leakage accordingly reliably.

BRIEF DESCRIPTION OF THE DRAWINGS

FIG. 6(A) a top plan view of an absorbent element 4A, and FIG. 6(B) is a top plan view of the absorbent 4 showing an overlapping state.

FIGS. 12(A) to 12(D) are manufacturing step diagrams showing modes of example, in which the individual absorbent elements 4A and 4B are enclosed with the crepe papers 5.

FIGS. 16(A) to 16(C) are back views of the sanitary napkin 1 showing a wiring pattern of pressure-sensitive adhesive layers 27 and 27.

DETAILED DESCRIPTION OF THE INVENTION

Figure 1:
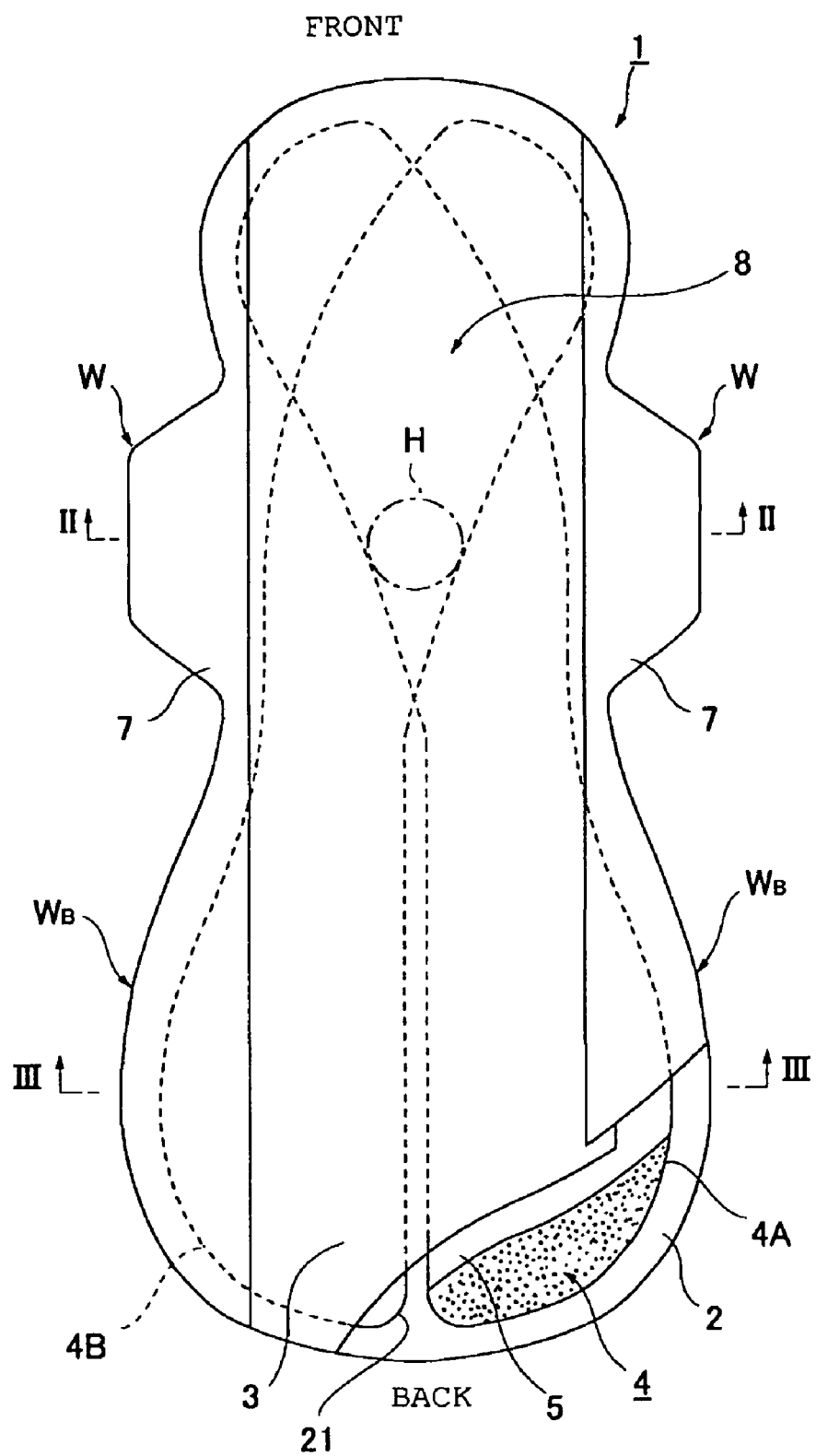
FIG. 1 is a development of a sanitary napkin 1 according to the invention.
Figure 2:
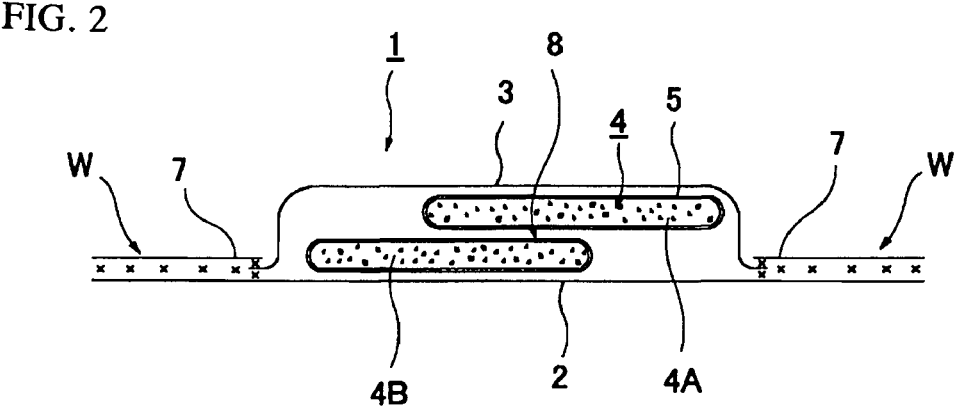
FIG. 2 is a view taken along line II-II of FIG. 1.
Figure 3:
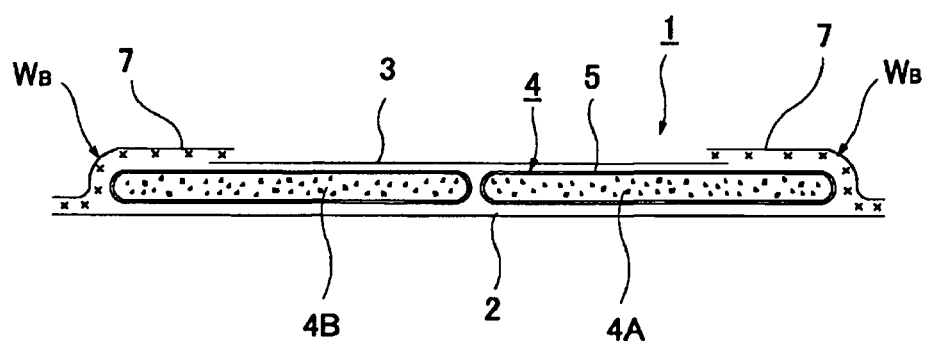
FIG. 3 is a view taken along line III-III of FIG. 1.

An embodiment of the invention is described in detail in the following with reference to the accompanying drawings. FIG. 1 is a development of a sanitary napkin 1 according to the invention; FIG. 2 is a view taken along line II-II of FIG. 1; and FIG. 3 is a view taken along line III-III of FIG. 1.

The sanitary napkin 1 is constituted mainly of a liquid-impermeable back sheet 2 made of a polyethylene sheet or the like, a liquid-permeable surface sheet 3 for causing menses, vaginal discharges and the like to permeate therethrough quickly, an absorbent 4 sandwiched between those two sheets 2 and 3 and made of cotton-like pulp, synthetic pulp or the like, and a crepe paper 5 enclosing the absorbent 4 so as to keep the shape of and improve the diffusivity of the absorbent 4. Around the absorbent 4, moreover, the outer edge portions of the liquid-impermeable back sheet 2 and the liquid-permeable surface sheet 3, or side nonwoven fabrics 7 are joined by an adhesive such as a hot-melt or adhering means such as a heat seal. Sideways protruding wing-shaped flaps W and W are formed of the laminated portions of the liquid-impermeable back sheet 2 and the side nonwoven fabrics 7 at the two side portions of a body liquid discharge portion H. Second wing-shaped flaps $W_B$ and $W_B$ are formed at the portions positioned closer to the buttock sides.

The structure of the sanitary napkin 1 is described in more detail in the following.

A sheet material having at least a water-barrier property, such as polyethylene or polypropylene is used for the liquid-impermeable back sheet 2. By securing the liquid impermeability substantially through a waterproof film, however, there can be used a nonwoven sheet (wherein the waterproof film and the nonwoven fabric constitute the liquid-impermeable back sheet) or the like. In recent years, there is a tendency that a moisture-permeable material is suitably used from the standpoint of preventing stuffiness. This water-barrier/moisture-permeable sheet material is properly exemplified by the finely porous sheet which is obtained by melting and kneading an inorganic filler in an olefin-group resin such as polyethylene or polypropylene thereby to form a sheet and then by elongating the sheet in one- or two-axis directions.

The surface sheet 3 is properly exemplified by a porous or non-porous nonwoven fabric or a porous plastic sheet. The material fibers constituting the nonwoven fabric can be not only synthetic fibers such as an olefin group, e.g., polyethylene or polypropylene, a polyester group or a polyamide group but also reproduced fibers such as rayon or cupra, or natural fibers such as cotton. It is also possible to use the nonwoven fabric which is obtained by a suitable working method such as a spun lacing method, a spun bonding method, a thermal bonding method, an air-through method, a melt-blown method or a needle punching method. Of these working methods: the spun lacing method is excellent in softness; the spun bonding method is excellent in the richness of drapability; and the thermal bonding method and the air-through method are excellent in bulkiness and softness.

The absorbent 4 sandwiched between the liquid-impermeable back sheet 2 and the surface sheet 3 is preferably made of cotton pulp. The absorbent 4 can also be exemplified by mixing a highly water-absorptive resin into the cotton pulp or by mixing not only chemical fibers but also the highly water-absorptive resin into the pulp. This pulp is exemplified by cellulose fibers such as chemical pulp or molten pulp made of wood, or artificial cellulose fibers such as rayon or acetate, and soft-wood pulp having longer fibers than those of hard-wood pulp is used preferably for functions and prices. In the shaping of the absorbent 4, it is possible to use the well-known method such as the fiber-stacking method or the air-laying method. The invention is especially effective for solving the problem that the thin-type absorbent shaped by the air-laying method is hard to follow the motions of the wearer's body.

The highly water-absorptive resin can be exemplified by crosslinked polyacrylate, self-crosslinked polyacrylate, saponified, crosslinked copolymer of acrylic ester-vinyl acetate, crosslinked copolymer of isobutylene-maleic anhydride, polysulphone acid base crosslinked material or partially crosslinked water-swelling polymer such as polyethylene oxide or polyacrylic amide. Of these, the preferred one is the acrylic acid or acrylate group which is excellent in the water absorption and the water absorbing rate. The highly water-absorptive resin having the water-absorbing performance can be adjusted in the water absorptivity and the water absorbing rate in its manufacturing process by adjusting the crosslinking density and the crosslinking density gradient. It is desired that the content of the highly water-absorptive resin is 10 to 60%. A sufficient absorptivity cannot be provided in case the content of the highly water-absorptive resin is less than 10%. In case the content is more than 60%, the pulp fibers are not entangled so that the sheet strength easily drops to cause tears, cracks or the like.

Especially in the invention, the absorbent 4 is constituted of one set of left and right absorbent elements 4A and 4B disposed generally along the longitudinal direction of the sanitary napkin 1, and is arranged to form an intersecting portion 8, at which the absorbent elements 4A and 4B intersect each other at a region containing the portion corresponding to at least the blood discharge opening H of the wearer. More specifically, the absorbent 4 is constituted of one set of the left and right absorbent elements arranged substantially along the longitudinal direction of the sanitary napkin 1. The absorbent element 4A of one side is formed into such a flat shape as is dogleg to the right in a top plan view whereas the absorbent element 4B of the other side is also formed into such a flat shape as is dogleg to the left in a top plan view, so that the absorbent elements 4A and 4B are arranged to intersect each other in at least the region which contains the portion of the blood discharge opening H of the wearer. Moreover, the individual absorbent elements 4A and 4B are so arranged in parallel at the back portion of the sanitary napkin 1 that they do not overlap each other at the widthwise central portion along the longitudinal direction. With the constitution thus far described, the intersecting portion 8, on which the absorbent elements 4A and 4B are stacked, contacts the body liquid discharge portion H closely to prevent the leakage reliably. Even if the back portion of the napkin is torsionally deformed by the motions of the buttocks, moreover, no twist occurs at the intersecting portion 8. At the same time, the easy deformations from the intersecting portion 8 in the oblique direction cause the individual absorbent elements 4A and 4B to follow the motions of the body so that the leakage of the body liquid can be reliably prevented.

On the other hand, the sanitary napkin 1 is provided, on the surface and at the two side portions, with the side nonwoven fabrics 7 and 7 along the longitudinal direction and substantially all over the entire length of the napkin 1. From the point of the function to be emphasized, the nonwoven fabric treated to be water-repellent or hydrophilic can be used as the side nonwoven fabrics 7. If the function to prevent the menses, vaginal discharge or the like from penetrating or to enhance the texture is emphasized, for example, it is desired to use the nonwoven fabric which has been treated to become water-repellent with coating a water-repellent of a silicone group, a paraffin group, an alkylchromic chloride group or the like. If the absorptivity of menses or the like is emphasized, on the other hand, it is desired, in order to use the hydrophilic nonwoven fabric which is made to be hydrophilic by applying a capillary phenomenon, to swell synthetic fibers or to make the same porous in the synthetic fiber manufacturing procedure by a method for polymerizing the synthetic fibers in the coexistence of a compound having hydrophilic radicals such as an oxidized product of polyethylene glycol, a method for treating with metallic salt such as stannic chloride so that the surface is partially molten and made porous thereby to deposit the metallic hydroxide or the like.

The side nonwoven fabrics 7 are adhered by an adhesive such as a hot-melt at the outer portions of the widthwise intermediate portions and throughout the ranges slightly over the side edges of the absorbent and to the outer edges of the liquid-impermeable back sheet 2, as shown in FIG. 2. Either the laminated seat portions between the side nonwoven fabrics 7 and the liquid-impermeable back sheet 2 or the laminated portions of the absorbent 4 between the side nonwoven fabrics 7 and the liquid-impermeable back sheet 2 form the paired left and right wing-shaped flaps W and W at the absorbent side positions corresponding substantially to the body liquid discharge portion H, and form the second wing-shaped flaps $W_B$ and $W_B$ at the positions closer to the buttock sides.

Figure 4:
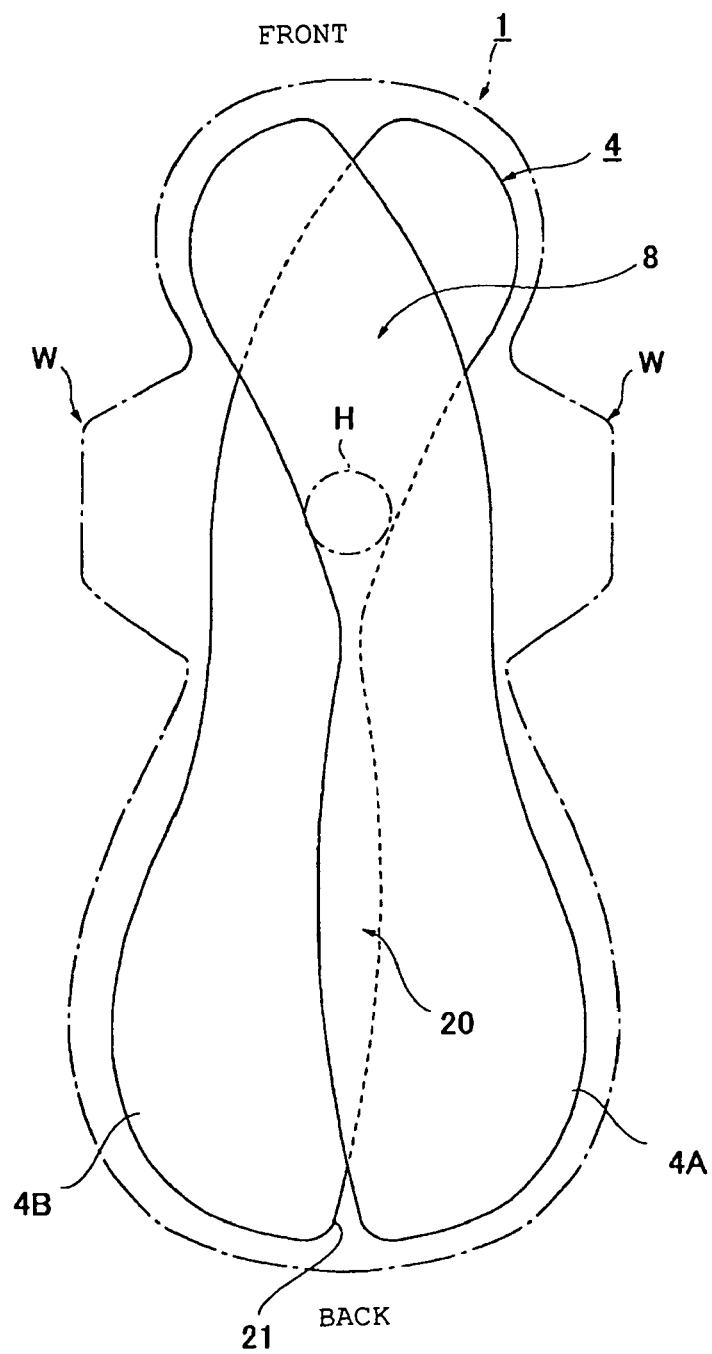
FIG. 4 is a top plan view showing another mode (1) of embodiment of an absorbent 4.

Next, specific examples are explained on the mode of the absorbent 4 of the sanitary napkin 1 according to the invention. In the aforementioned mode of embodiment, the absorbent elements 4A and 4B are so arranged in parallel at the back portion that they do not overlap each other at the widthwise central portion along the longitudinal direction. As shown in FIG. 4, the individual absorbent elements 4A and 4B are arranged to form such an overlap portion 20 at the back portion of the sanitary napkin 1 that they overlap each other at the widthwise central portion along the longitudinal direction. Here, the individual absorbent elements 4A and 4B in that overlap portion 20 may have a thickness equivalent to that of the other portions, but are preferably thinner than the other portion from the view point of suppressing the rigidity of the absorbent 4 at a low level.

Moreover, it is preferred that the absorbent 4 is made the narrowest at the portion corresponding to the crotch of the wearer while the individual absorbent elements 4A and 4B being assembled, as shown in FIG. 1. As a result, the present sanitary napkin 1 can fit the legs of the wearer with no uncomfortable feeling.

Figure 5:
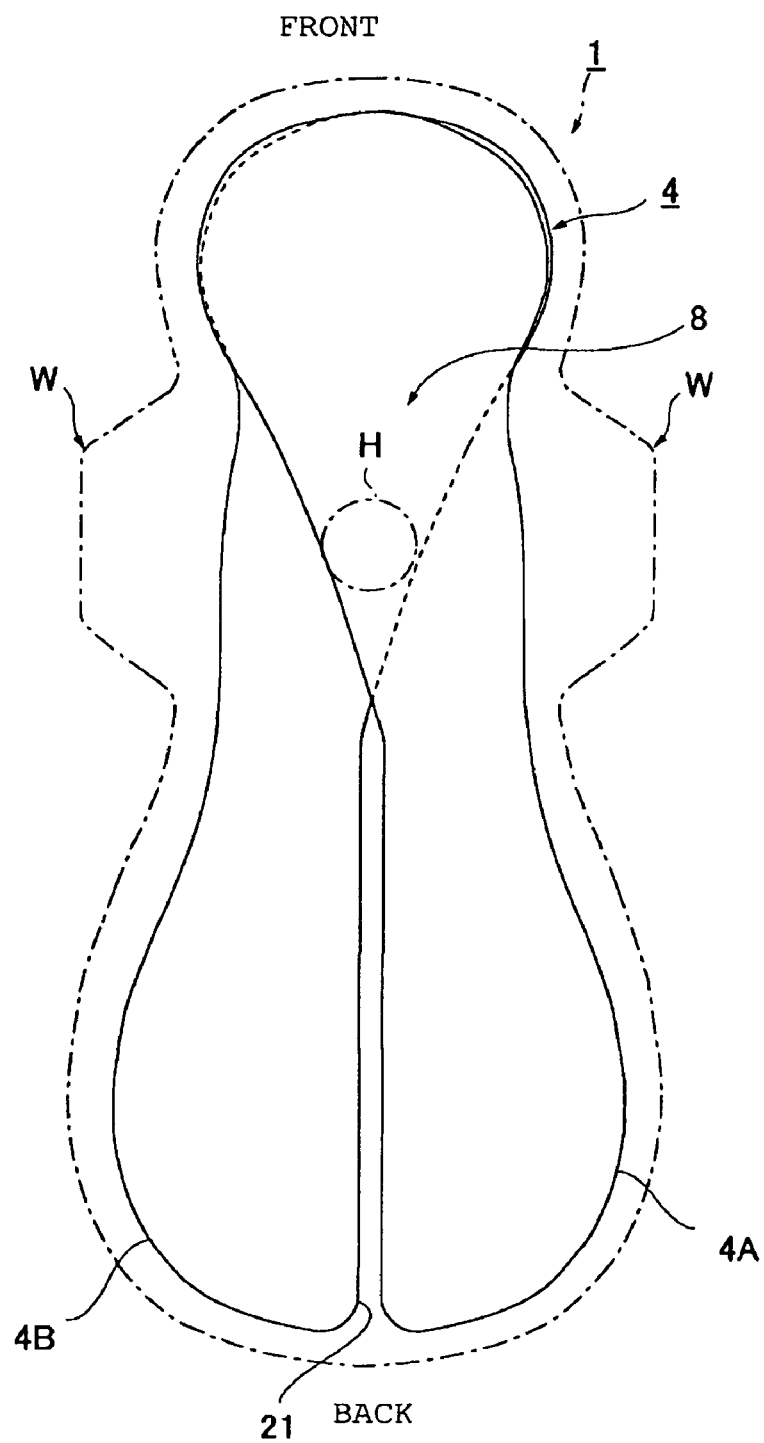
FIG. 5 is a top plan view showing another mode (2) of embodiment of the absorbent 4.

As shown in FIG. 5, moreover, the absorbent 4 may be formed such that the individual absorbent elements 4A and 4B are arranged to overlap substantially coextensively in the region of the sanitary napkin 1 on the front side of the portion corresponding to the blood discharge opening H of the wearer. The absorbent of the front portion is made of the double structure so that the front portion can absorb the body liquid more and can be more rigid. Even if a torsional deformation occurs in the back portion of the napkin, therefore, the napkin does not get twisted at its front portion so that it can be reliably kept in close contact with the body.

Figure 6A:
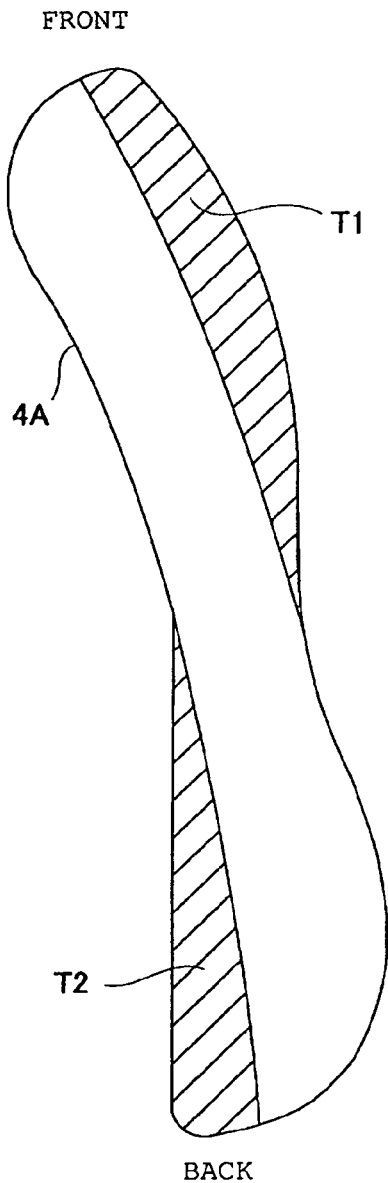
FIGS. 6(A) and 6(B) are top plan views showing another mode (3) of embodiment of the absorbent 4.
Figure 6B:
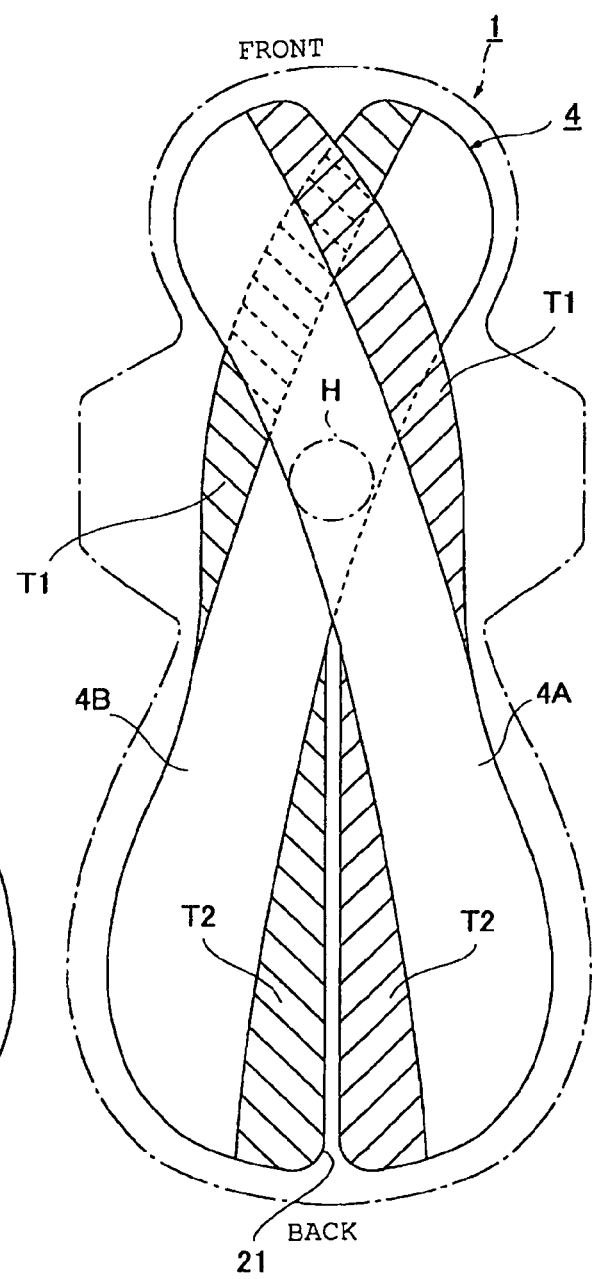

As shown in FIGS. 6(A) and 6(B), moreover, the individual absorbent elements 4A and 4B can be made thinner at an outer edge portion T1 in the front portion of the sanitary napkin 1 and at an inner edge portion T2 in the back portion of the sanitary napkin 1 than the remaining portions. As a result, with the individual absorbent elements 4A and 4B being assembled, as shown in FIG. 6(B), the absorbent elements 4A and 4B made to have the ordinary thickness are overlapped in the region containing the body liquid discharge portion H, thereby to retain the absorbing performance in the body liquid discharge portion H. In the leg surrounding portions of the two side portions of the body liquid discharge portion H, moreover, the absorbents of the outer edge portions T1 and T2 are made thin to give no uncomfortable feeling around the legs of the wearer when worn. In addition, the absorbents of the inner edge portions T2 and T2 on the back portion are made thin so that they can be easily fitted in the groove between the buttocks.

Here is described the means for fitting the sanitary napkin in the groove of the buttocks so as to prevent the leakage of the body liquid from the back side. As shown in FIG. 1 and so on, the first means is exemplified by cutting off the corners of the back end portions of the sides confronting the paired absorbent elements 4A and 4B and by forming a notch 21 at the center of the back end portion of the absorbent 4 while the individual absorbent elements 4A and 4B being combined. This notch 21 makes a mountain fold easily, when the notch 21 is pinched on the two sides by the fingers of the wearer, so that the napkin can be fitted at its back portion in the groove between the buttocks.

Figure 7:
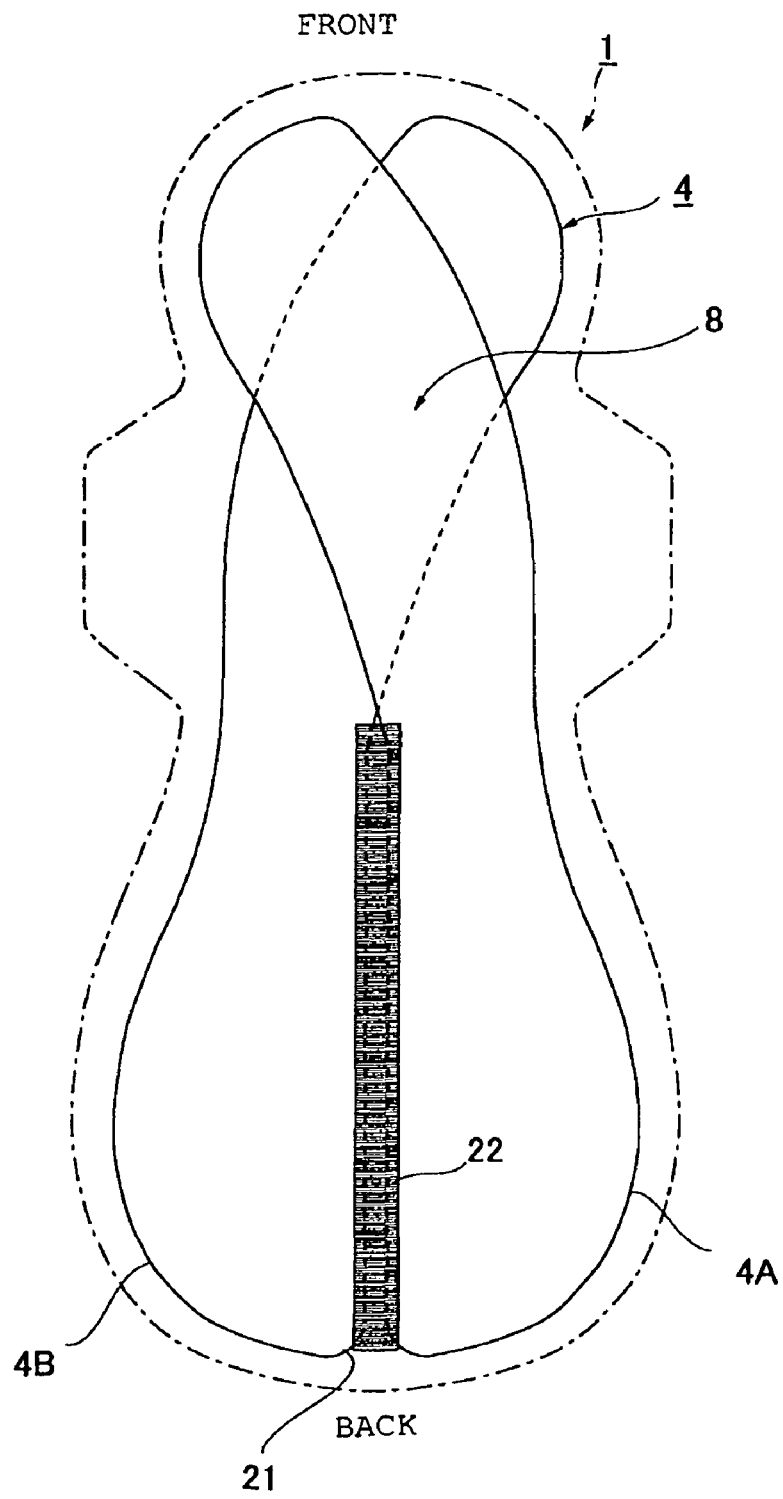
FIG. 7 is a top plan view of the absorbent 4 showing the arranged state of an elastic member 22.

As shown in FIG. 7, the second means is exemplified by arranging an elastic member 22 at the absorbent center along the longitudinal direction at the back portion of the sanitary napkin 1 between the back sheet 2 and the absorbent 4 while the individual absorbent elements 4A and 4B being combined. By the stretching force of the elastic member 22, the back portions of the sanitary napkin 1 can be deformed along the groove between the buttocks so that they can be easily fitted in the groove between the buttocks.

Figure 8:
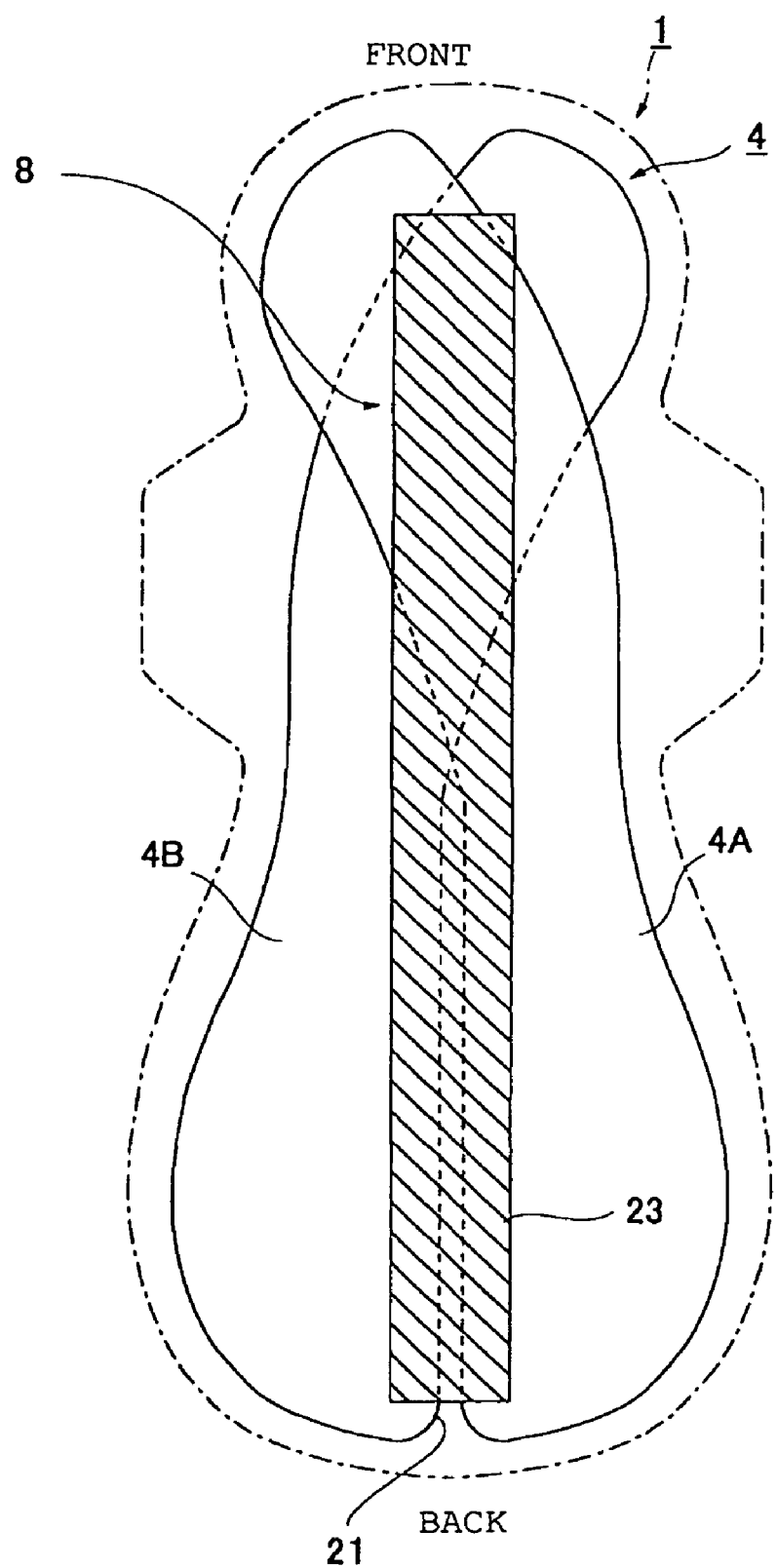
FIG. 8 is a top plan view of the absorbent 4 showing the arranged state of a second sheet 23.

Here is described the means which can be applied to the sanitary napkin 1 of the invention so as to prevent the leakage of the body liquid more reliably. In the sanitary napkin 1 according to the invention, as shown in FIG. 8, a hydrophilic second sheet 23 is preferably arranged at the widthwise center along the longitudinal direction while the individual absorbent elements 4A and 4B being combined. By arranging the second sheet 23, the body liquid can be quickly transferred to the absorbent 4 from the front portion to the back portion, thereby to prevent the leakage.

Figure 9:
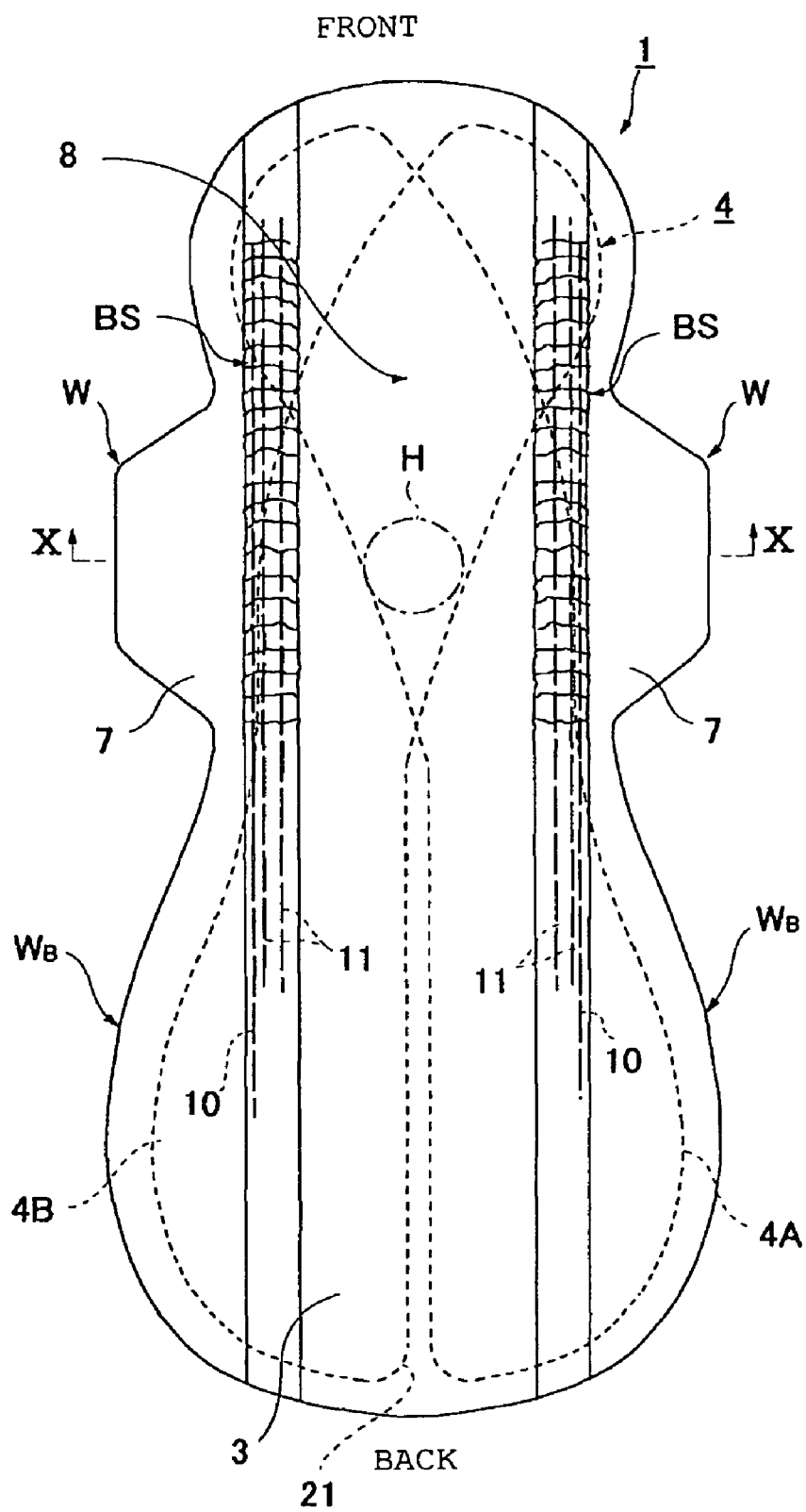
FIG. 9 is a development of the sanitary napkin 1 showing the arranged state of stereo gathers BS.
Figure 10:
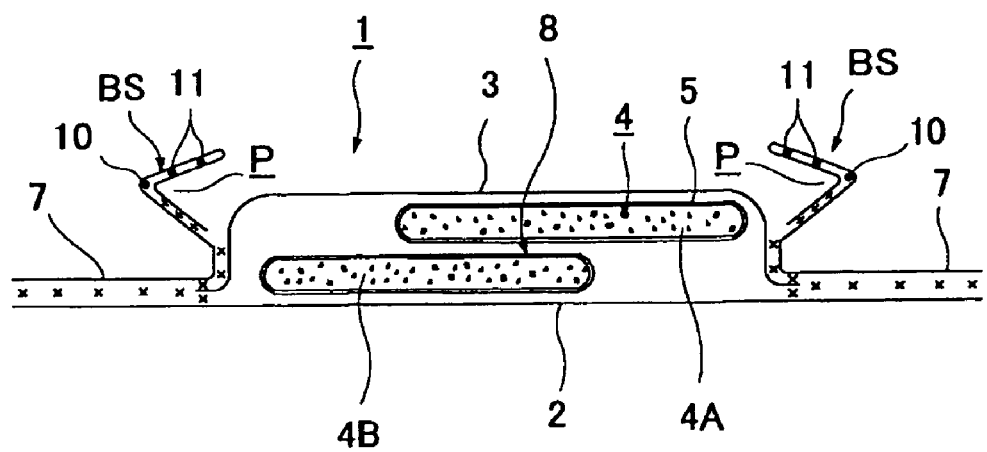
FIG. 10 is a view taken along line X-X of FIG. 9.

As shown in FIG. 9 and FIG. 10, moreover, the sanitary napkin 1 according to the invention may be provided with stereo gathers BS and BS, which are raised from the two side portions of the using face thereof by the shrinking forces of elastic stretching members. In this case, the stereo gathers BS are raised only within the ranges corresponding to the intersecting portion 8 of the individual absorbent elements.

The stereo gathers BS are formed by folding back the inner portions of the side nonwoven fabrics 7 substantially doubly, by arranging such filament-like elastically extensible members 10 in the double sheets that they are fixed at two ends or at longitudinally suitable positions in the intermediate portions of the height direction, and by arranging a plurality of or two filament-like elastically extensible members 11 and 11 on the upper side portions of the filament-like elastically extensible members 10 in the shown embodiment such that they are fixed at two ends or at suitable longitudinal positions. These double sheet portions are so adhered at their front end back ends to the sides of the absorbents 4 that they are folded and laminated in the Z-shaped section. As a result, the stereo gathers BS and BS rising from the surface side are formed such that pockets P and P are opened inward in bent sections at the portions arranging the filament-like elastically extensible members 10.

The stereo gathers BS and BS are constituted of the side nonwoven fabrics 7 different from the liquid-permeable surface sheet 3, such as the nonwoven fabric material which has been subjected to a suitable water-repelling treatment or a hydrophilic treatment in accordance with the purpose to prevent the penetration of menses, vaginal discharge or the like or to enhance the texture. Those side nonwoven fabrics 7 to be used can be formed by subjecting the material of natural fibers, synthetic fibers or reproduced fibers to a suitable processing method. In order to eliminate the stiffness and to prevent the stuffiness, it is advisable to use the nonwoven fabric which is made air-permeable by suppressing a basis weight. Specifically, it is desirable to use the nonwoven fabric which has been manufactured to have the basis weight of 18 to 23 $g/m^2$. The permeation of the body liquid is reliably prevented by using the nonwoven fabric which has been treated with coating the water-repellent of a silicone group, a paraffin group or an alkylchromic chloride group.

Figure 11A:
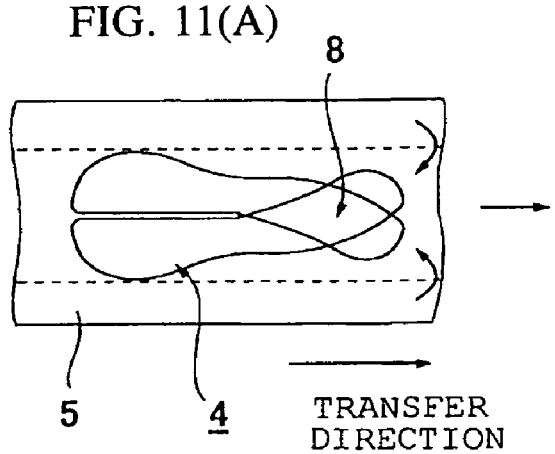
FIGS. 11(A) to 11(C) are manufacturing step diagrams showing modes of example, in which the absorbent 4 is enclosed with a crepe paper 5.
Figure 11B:
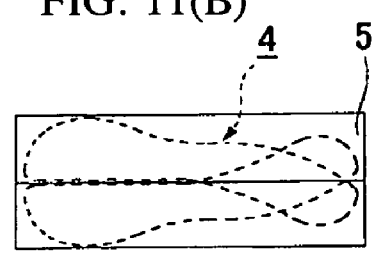
Figure 11C:
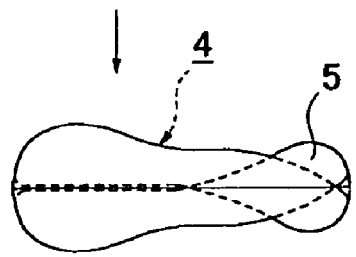
Figure 13A:
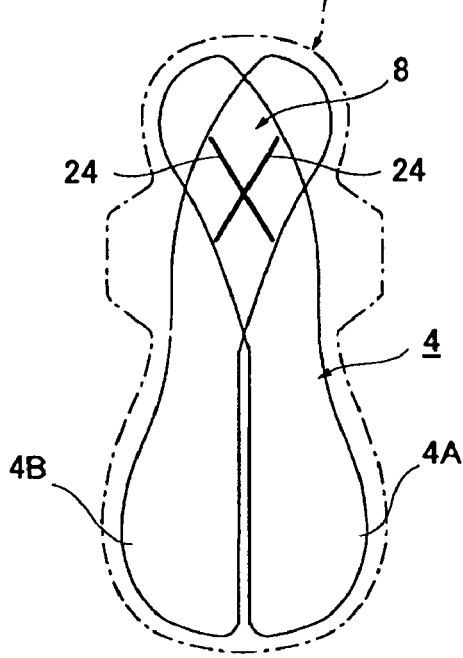
FIGS. 13(A) to 13(D) are plan views of the absorbent 4 showing patterns for embossing at emboss 24 in an intersecting portion 8.
Figure 13B:
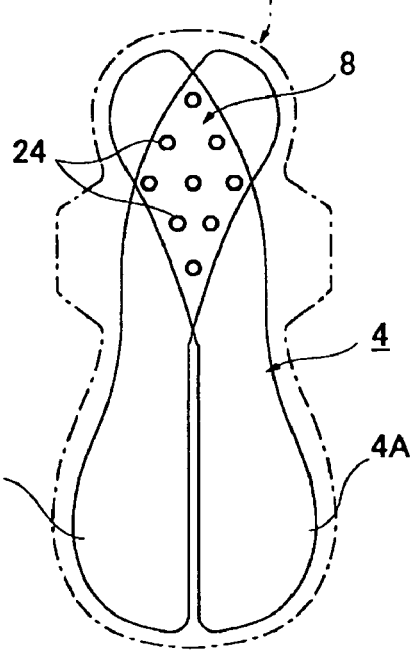
Figure 13C:
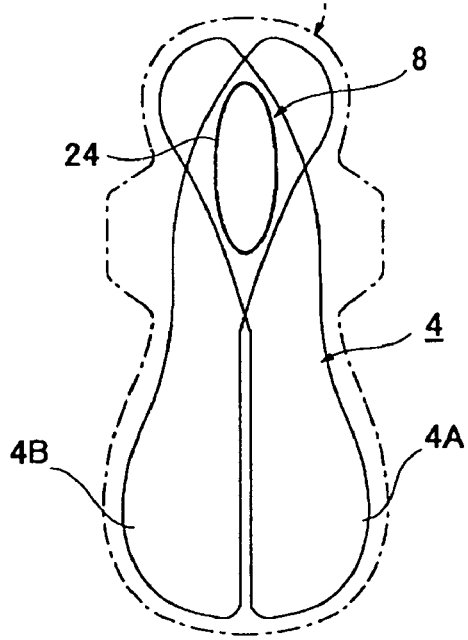
Figure 13D:
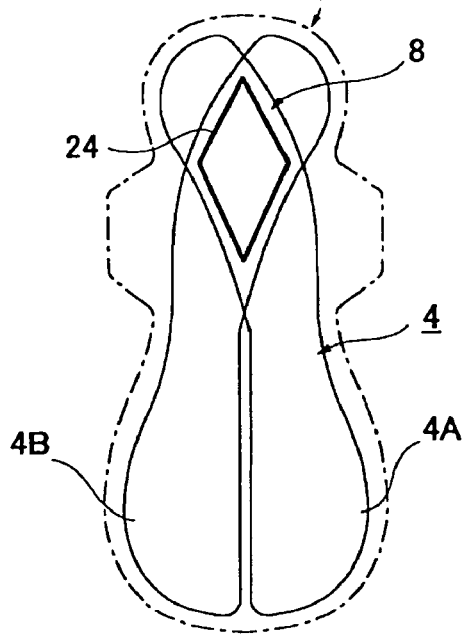

Next, methods for enclosing the absorbent 4 with the crepe paper 5 are described on the basis of FIGS. 11(A) to 11(C) and FIG. 12. FIGS. 11(A) to 11(C) present diagrams showing the manufacturing steps of the case, in which the individual absorbent elements 4A and 4B are integrally enclosed in combined states by the crepe paper. In this case, as shown in FIG. 11(A), the individual absorbent elements 4A and 4B are placed in the combined state on the widthwise center of the crepe paper 5 let off the crepe paper roll (although not shown). After this, the crepe paper 5 is folded at its two widthwise sides on the absorbent 4, and these folded portions are individually cut (as referred to FIG. 11(B)). As shown in FIG. 11(C), moreover, the crepe paper 5 is cut along the periphery of the absorbent 4, and this absorbent 4 is transferred to the next manufacturing step.

On the other hand, FIGS. 12(A) to 12(D) present diagrams showing the manufacturing steps of the case, in which the individual absorbent elements are individually enclosed by the crepe papers. In this case, as shown in FIG. 12(A), the individual absorbent elements 4A and 4B are individually placed on the widthwise centers of the crepe papers 5 let off the crepe paper rolls (although not shown). After this, the crepe papers 5 are individually folded at their two widthwise sides on the absorbent elements 4A and 4B, and these folded portions are individually cut (as referred to FIG. 12(B)). As shown in FIG. 12(C), moreover, the absorbent elements 4A and 4B, which are individually enclosed by the crepe papers 5, are combined with each other. After this, the crepe paper 5 are cut along the periphery of the absorbent 4, as shown in FIG. 12(D), and the assembly is transferred to the next manufacturing step.

In the invention, moreover, the individual absorbent elements 4A and 4B need not be enclosed by the crepe papers but may be interposed directly between the surface sheet 3 and the back sheet 2. The present embodiment is preferable, because the interposition of the crepe paper raises the apparent bending resistance of the absorbent so that the followability to the motions of the body is not obstructed and because the crepe paper is interposed so that the penetration rate of the body liquid does not drop.

Here, the absorbent elements 4A and 4B are joined at the intersecting portion 8 between the individual absorbent elements 4A and 4B by adhering means such as a hot-melt adhesive or joining means such as embossing means. Especially in the invention, the joining strength at the intersecting portion 8 has to be retained to such an extent that the deformation at the napkin back portion may not exert the influences such as the twist of the front portion. For this necessity, it is preferred that the absorbent elements 4A and 4B are joined to each other by the joining means for embossing at 24 from the upper face side. In this case, the embossing pattern 24 at the intersecting portion 8 can be made, as shown in FIGS. 13(A) to 13(D), in various modes including FIG. 13(A) a straight cross shape, FIG. 13(B) a dot shape, FIG. 13(C) a circular shape, and FIG. 13(D) a polygonal shape (e.g., a rhomboid shape).

The sanitary napkin 1 according to the invention can have a plurality of stripes of pressure-sensitive adhesive layers 25, 25, . . . , and so on formed on the outer face of the back sheet 2 so as to adhere the sanitary napkin 1 to the shorts. The pressure-sensitive adhesive to be employed for forming the pressure-sensitive adhesive layers 25, 25, . . . , and so on is properly composed mainly of any of a styrene-group polymer, an adhesion applying agent and a plasticizer, for example. The styrene-group polymer can be exemplified by a block copolymer of styrene-ethylene-butylene-styrene, a copolymer of styrene-butylene-styrene, and a copolymer of styrene-isobutylene-styrene, of which one kind or a polymer blend of two kinds or more can be used. Of these, the block copolymer of styrene-ethylene-butylene-styrene is preferred for an excellent thermal stability. Moreover, the adhesion-applying agent and the plasticizer to be preferably used is solid at the room temperature. The adhesion-applying agent is exemplified by a C5-group petroleum resin, a C9-group petroleum resin, a dicyclopentadiene-group petroleum resin, a rosin-group petroleum resin, a polyterpene resin or a terpene phenol resin. The plasticizer is exemplified by a monomer plasticizer such as triphenyl phosphate, dibutyl phthalate or dioctyl phthalate, or a polymer plasticizer such as a vinyl polymer or polyester.

Figure 14:
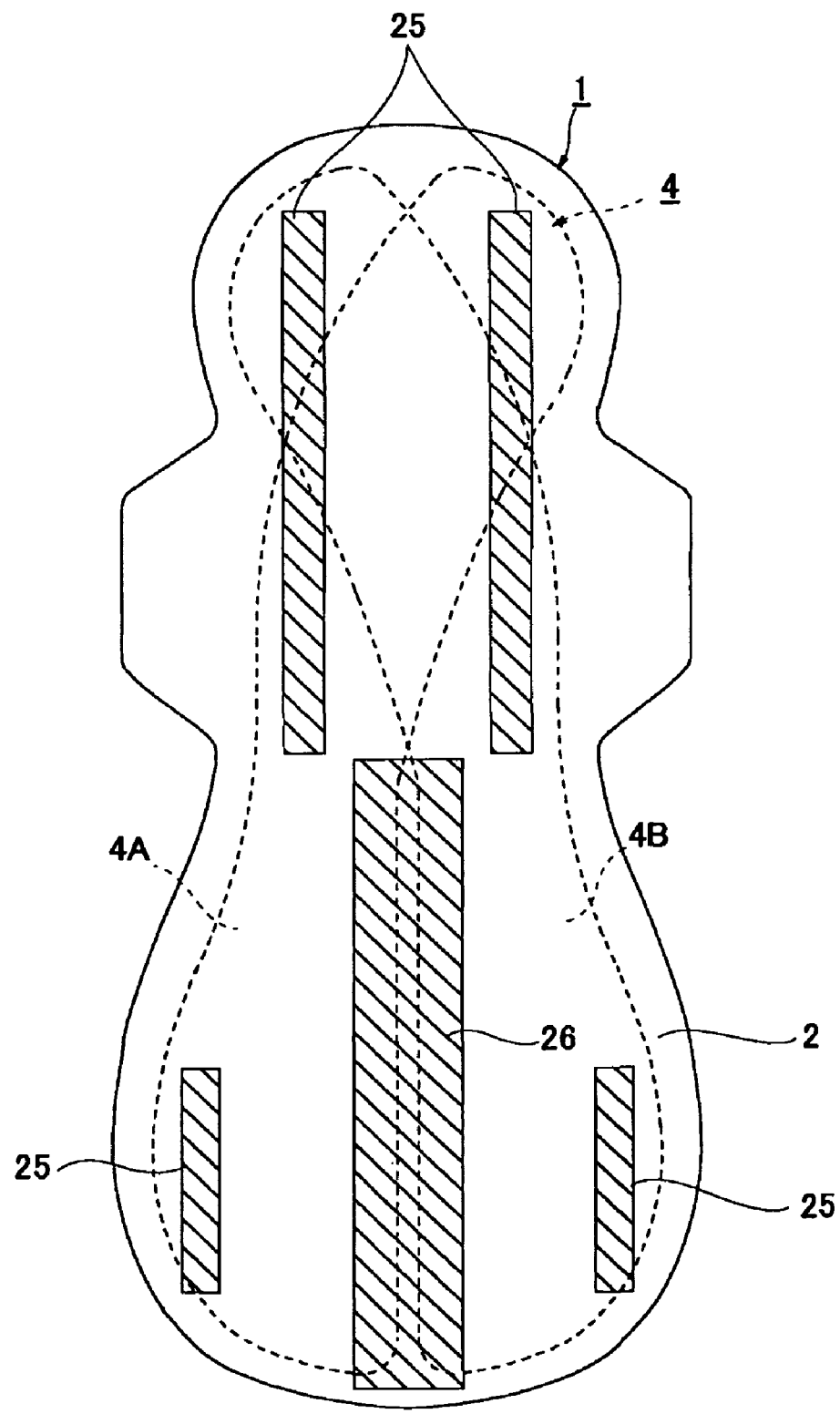
FIG. 14 is a back view of the sanitary napkin 1 showing a wiring pattern (1) of pressure-sensitive adhesive layers 25 and 26.
Figure 15:
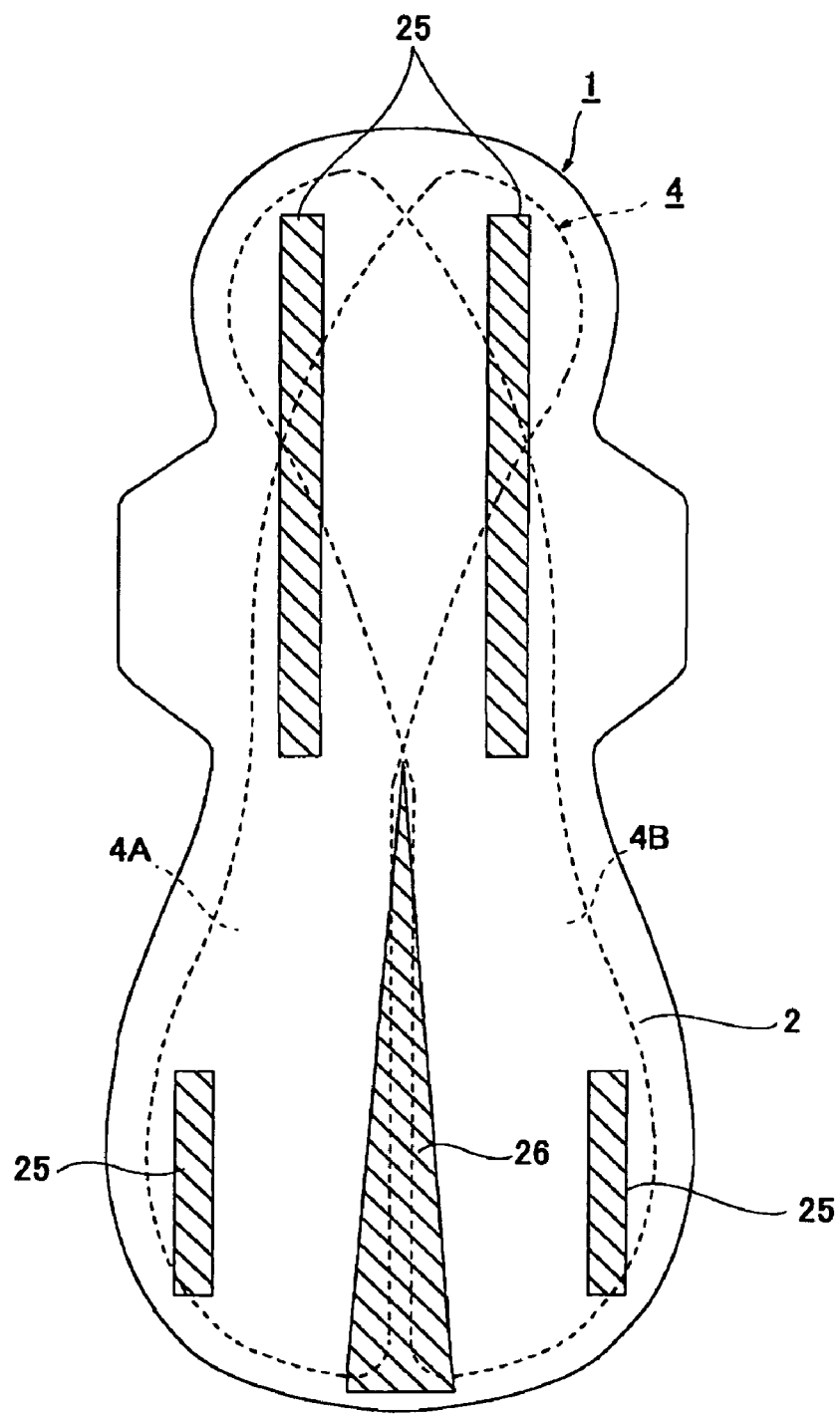
FIG. 15 is a back view of the sanitary napkin 1 showing a wiring pattern (2) of the pressure-sensitive adhesive layers 25 and 26.

Especially in the invention, as shown in FIG. 14 and FIG. 15, one of the plural stripes of pressure-sensitive adhesive layers is a pressure-sensitive adhesive layer 26 extending along the longitudinal direction at the widthwise central portion in the back portion of the sanitary napkin 1. The pressure-sensitive adhesive layer 26 has its mountain-folded portions adhered, when the back portion of the sanitary napkin 1 is pinched and mountain-folded to the using face by the fingers of the wearer, to each other so that the pressure-sensitive adhesive layer 26 is kept in the mountain-folded state. This pressure-sensitive adhesive layer 26 may also be formed into a triangular shape to become gradually narrower from the back portion to the central portion of the napkin 1 so that it may fit the groove shape of the buttocks better, as shown in FIG. 15.

As shown in FIGS. 16(A) to 16(C), moreover, the back sheet 2 can be provided on its outer face with at least two stripes of pressure-sensitive adhesive layers 27 and 27 to be adhered to the shorts, such that the pressure-sensitive adhesive layers 27 and 27 extend along the individual absorbent elements 4A and 4B and intersect with each other at the portion corresponding substantially to the blood discharge opening H of the wearer. This case is preferable, because the pressure-sensitive adhesive layers 27 and 27 do not obstruct the motions of the absorbent to accompany the torsional deformations of the body but can prevent the displacements from the shorts. The wiring pattern of the body displacement preventing pressure-sensitive adhesive layers 27 and 27 can be exemplified by various modes such as a straight cross shape, as shown in FIG. 16(A), or a bent cross shape, as shown in FIG. 16(B). As shown in FIG. 16(C), moreover, the pressure-sensitive adhesive layers 27 and 27 may also be arranged in combination with the pressure-sensitive adhesive layer 26 to be fitted in the aforementioned groove between the buttocks.

The invention claimed is:

1. An absorbent article for a female wearer, comprising a front portion and a back portion and an absorbent interposed between a liquid-permeable surface sheet and a back sheet, wherein said absorbent comprises a set of left and right separate, individual and absorbent elements arranged substantially along a longitudinal direction of the absorbent article, the set of left and right absorbent elements being arranged so as to have overlaid intersecting portions at a region containing a portion corresponding substantially to a blood discharge opening of the wearer, a respective forward end and a respective rearward end of the left absorbent element being arranged on respectively opposite sides of the absorbent article along the longitudinal direction of the absorbent article so that the respective forward and rearward ends are disposed on said respectively opposite sides of the absorbent article about a longitudinal axis thereof, a respective forward end and a respective rearward end of the right absorbent element being arranged on respectively opposite sides of the absorbent article along the longitudinal direction of the absorbent article so that the respective forward and rearward ends are disposed on said respectively opposite sides of the absorbent article about a longitudinal axis thereof, and when viewed in a top plan view, the absorbent elements each constitute a bent flat shape in which each of the left and right absorbent elements defines a curved portion, the curved portions each comprising a substantially entirely curved peripheral section and opposing each other about the longitudinal axis of the absorbent article so as to extend the entirely curved peripheral section of each curved portion of each absorbent element toward each other beginning at the region containing the portion corresponding to the blood discharge opening of the wearer and away from each other at the front portion of the absorbent article, said extension defining a terminal point of intersection substantially adjacent an outer peripheral end of the front portion of the absorbent article and a terminal point of intersection substantially below the region containing the portion corresponding to the blood discharge opening of the wearer that are each coincident with the longitudinal axis of the absorbent article, and whereby at the rear of the absorbent article, at a widthwise central portion of the absorbent article, the absorbent elements are arranged parallel to each other along the longitudinal direction of the absorbent article so that said arrangement of the set of left and right absorbent elements substantially resists twisting of the absorbent elements at their overlaid intersecting portions in the area of the region containing the portion corresponding substantially to the blood discharge opening of the wearer while allowing remaining portions of the absorbent elements to move according to a motion of the wearer in order to substantially prevent leakage of body liquid from between the wearer of the absorbent article and the absorbent article when the absorbent article is worn.

2. An absorbent article comprising a front portion and a back portion and an absorbent interposed between a liquid-permeable surface sheet and a back sheet, wherein said absorbent comprises a set of left and right separate, individual and unitary absorbent elements, the set of left and right absorbent elements being arranged so as to have overlaid intersecting portions substantially along a longitudinal direction of the absorbent article, a respective forward end and a respective rearward end of the left absorbent element being arranged on respectively opposite sides of the absorbent article along the longitudinal direction of the absorbent article so that the respective forward and rearward ends are disposed on said respectively opposite sides of the absorbent article about a longitudinal axis thereof, a respective forward end and a respective rearward end of the right absorbent element being arranged on respectively opposite sides of the absorbent article along the longitudinal direction of the absorbent article so that the respective forward and rearward ends are disposed on said respectively opposite sides of the absorbent article about a longitudinal axis thereof, and one of the left and right absorbent elements forms a bent flat shape to the right in a top plan view whereas the other of the left and right absorbent elements forms a bent flat shape to the left in a top plan view, so that the absorbent elements are arranged to intersect each other in at least a region corresponding substantially to a blood discharge opening of the wearer and in which each of the left and right absorbent elements defines curved portion, the curved portions each comprising a substantially entirely curved peripheral section and opposing each other about the longitudinal axis of the absorbent article so as to extend the entirely curved peripheral section of each curved portion of each absorbent element toward each other beginning at the region containing the portion corresponding to the blood discharge opening of the wearer and away from each other at the front portion of the absorbent article, said extension defining a terminal point of intersection substantially adjacent an outer peripheral end of the front portion of the absorbent article and a terminal point of intersection substantially below the region containing the portion corresponding to the blood discharge opening of the wearer that are each coincident with the longitudinal axis of the absorbent article, and whereby at the rear of the absorbent article, the absorbent elements are arranged parallel to each other along the longitudinal direction of the absorbent article so that said arrangement of the set of left and right absorbent elements substantially resists twisting of the absorbent elements at their overlaid intersecting portions in the area of the region containing the portion corresponding substantially to the blood discharge opening of the wearer while allowing remaining portions of the absorbent elements to move according to a motion of the wearer in order to substantially prevent leakage of body liquid from between the wearer of the absorbent article and the absorbent article when the absorbent article is worn.

3. An absorbent article as set forth in claim 1 or 2, wherein said left and right absorbent elements are so arranged in parallel at a back portion of said absorbent article that they have no portion overlapping each other at a widthwise central portion along the longitudinal direction of the back portion.

4. An absorbent article as set forth in claim 1 or 2, wherein said left and right absorbent elements are arranged to have such an overlap portion at a back portion of said absorbent article that they overlap each other at a widthwise central portion along the longitudinal direction of the back portion.

5. An absorbent article as set forth in claim 1 or 2, wherein the portion corresponding to the crotch of the wearer is the narrowest in a thickness direction along the longitudinal direction of the absorbent article.

6. An absorbent article as set forth in claim 1 or 2, wherein the left and right absorbent elements are arranged to overlap substantially coextensively in a region of the absorbent article on the front side of the portion corresponding to the blood discharge opening of the wearer.

7. An absorbent article as set forth in claim 1 or 2, wherein the back end portions of opposed sides of the absorbent elements are formed with cut off corners so that a notch is formed at a center of a back end portion of the absorbent article.

8. An absorbent article as set forth in claim 1 or 2, wherein an elastic member is arranged at an absorbent center along the longitudinal direction at a back portion of the absorbent article between the back sheet and the absorbent.

9. An absorbent article as set forth in claim 1 or 2, wherein a hydrophilic sheet is arranged at the widthwise center along the longitudinal direction.

10. An absorbent article as set forth in claim 1 or 2, further comprising elastic stretching members and stereo gathers raised by contraction forces of the elastic stretching members from two side portions of a face of the absorbent article intended for contact with the wearer, wherein said stereo gathers are raised adjacent the intersection of said individual absorbent elements.

11. An absorbent article as set forth in claim 1 or 2, further comprising respective crepe papers enclosing respective ones of the absorbent elements.

12. An absorbent article as set forth in claim 1 or 2, wherein said absorbent elements are interposed directly between and in contact with the surface sheet and the back sheet.

13. An absorbent article as set forth in claim 1 or 2, wherein said absorbent elements are joined to each other by embossing from the surface sheet at a region of intersection of said left and right absorbent elements.

14. An absorbent article as set forth in claim 1 or 2, further comprising a plurality of stripes of pressure-sensitive adhesive layers formed on an outer face of said back sheet so that they may be adhered to panties of the wearer, wherein one of said plural stripes of the pressure-sensitive adhesive layers is formed along the longitudinal direction at a widthwise central portion in a back side portion of said absorbent article.

15. An absorbent article as set forth claim 1 or 2, comprising at least two stripes of pressure-sensitive adhesive layers formed on an outer face of the back sheet and adapted to be adhered to panties of the wearer, wherein said pressure-sensitive adhesive layers extend along the left and right absorbent elements and intersect with each other at the portion corresponding substantially, to the blood discharge opening of the wearer.

16. An absorbent article for a female wearer, comprising a front portion and a back portion and an absorbent interposed between a liquid-permeable surface sheet and a back sheet, wherein said absorbent comprises a set of left and right separate, individual and unitary absorbent elements arranged substantially along a longitudinal direction of the absorbent article, the set of left and right absorbent elements being arranged so as to have overlaid intersecting portions at a region containing a portion corresponding substantially to a blood discharge opening of the wearer, a respective forward end and a respective rearward end of the left absorbent element being arranged on respectively opposite sides of the absorbent article along the longitudinal direction of the absorbent article so that the respective forward and rearward ends are disposed on said respectively opposite sides of the absorbent article about a longitudinal axis thereof, a respective forward end and a respective rearward end of the right absorbent element being arranged on respectively opposite sides of the absorbent article along the longitudinal direction of the absorbent article so that the respective forward and rearward ends are disposed on said respectively opposite sides of the absorbent article about a longitudinal axis thereof, and when viewed in a top plan view, the absorbent elements each constitute a bent flat shape in which each of the left and right absorbent elements defines a curved portion, the curved portions each comprising a substantially entirely curved peripheral section and opposing each other about the longitudinal axis of the absorbent article so as to extend the entirely curved peripheral section of each curved portion of each absorbent element toward each other beginning at the region containing the portion corresponding to the blood discharge opening of the wearer and away from each other at the front portion of the absorbent article, said extension defining a terminal point of intersection substantially adjacent an outer peripheral end of the front portion of the absorbent article and a terminal point of intersection substantially below the region containing the portion corresponding to the blood discharge opening of the wearer that are each coincident with the longitudinal axis of the absorbent article, and whereby at the rear of the absorbent article, at a widthwise central portion of the absorb t article, absorbent elements are arranged parallel to each other along the longitudinal direction of the absorbent article so that said arrangement of the set of left and right absorbent elements substantially resists twisting of the absorbent elements at their overlaid intersecting portions in the area of the region containing the portion corresponding substantially to the blood discharge opening of the wearer while allowing remaining portions of the absorbent elements to move according to a motion of the wearer in order to substantially prevent leakage of body liquid from between the wearer of the absorbent article and the absorbent article when the absorbent article is worn, the individual absorbent elements being thinner at an outer edge portion in a front portion of the absorbent article and at an inner edge portion in a back portion than at remaining portions thereof, in a longitudinal, width and thickness direction of the absorbent article.

17. An absorbent article comprising a front portion and a back portion and an absorbent interposed between a liquid-permeable surface sheet and a back sheet, wherein said absorbent comprises a set of left and right separate, individual and unitary absorbent elements, the set of left and right absorbent elements being arranged so as to have overlaid intersecting portions substantially along a longitudinal direction of the absorbent article, a respective forward end and a respective rearward end of the left absorbent element being arranged on respectively opposite sides of the absorbent article along the longitudinal direction of the absorbent article so that the respective forward and rearward ends are disposed on said respectively opposite sides of the absorbent article about a longitudinal axis thereof, a respective forward end and a respective rearward end of the right absorbent element being arranged on respectively opposite sides of the absorbent article along the longitudinal direction of the absorbent article so that the respective forward and rearward ends are disposed on said respectively opposite sides of the absorbent article about a longitudinal axis thereof, and one of the left and right absorbent elements forms a bent flat shape to the right in a top plan view whereas the other of the left and right absorbent elements forms a bent flat shape to the left in a top plan view, so that the absorbent elements are arranged to intersect each other in at least a region corresponding substantially to a blood discharge opening of the wearer and in which each of the left and right absorbent elements defines a curved portion, the curved portions each comprising a substantially entirely curved peripheral section and opposing each other about the longitudinal axis of the absorbent article so as to extend the entirely curved peripheral section of each curved portion of each absorbent element toward each other beginning at the region containing the portion corresponding to the blood discharge opening of the wearer and away from each other at the front portion of the absorbent article, said extension defining a terminal point of intersection substantially adjacent an outer peripheral end of the front portion of the absorbent article and a terminal point of intersection substantially below the region containing the portion corresponding to the blood discharge opening of the wearer that are each coincident with the longitudinal axis of the absorbent article, and whereby at the rear of the absorbent article, the absorbent elements are arranged parallel to each other along the longitudinal direction of the absorbent article so that said arrangement of the set of left and right absorbent elements substantially resists twisting of the absorbent elements at their overlaid intersecting portions in the area of the region containing the portion corresponding substantially to the blood discharge opening of the wearer while allowing remaining portions of the absorbent elements to move according to a motion of the wearer in order to substantially prevent leakage of body liquid from between the wearer of the absorbent article and the absorbent article when the absorbent article is worn, the individual absorbent elements being thinner at an outer edge portion in a front portion of the absorbent article and at an inner edge portion in a back portion than at remaining portions thereof, in a longitudinal, width and thickness direction of the absorbent article.

\* \* \* \* \*